US009957548B2

(12) United States Patent
Gerdes et al.

(10) Patent No.: US 9,957,548 B2
(45) Date of Patent: May 1, 2018

(54) METHODS OF CAPTURING SPERM NUCLEIC ACIDS

(71) Applicant: General Electric Company, Schenectady, NY (US)

(72) Inventors: Michael John Gerdes, Albany, NY (US); John Richard Nelson, Clifton Park, NY (US); Patrick McCoy Spooner, Slingerlands, NY (US); Ralf Lenigk, Niskayuna, NY (US)

(73) Assignee: GENERAL ELECTRIC COMPANY, Schenectady, NY (US)

( * ) Notice: Subject to any disclaimer, the term of this patent is extended or adjusted under 35 U.S.C. 154(b) by 185 days.

(21) Appl. No.: 14/672,358

(22) Filed: Mar. 30, 2015

(65) Prior Publication Data

US 2016/0289735 A1 Oct. 6, 2016

(51) Int. Cl.
 *C12Q 1/68* (2018.01)
 *C12N 15/10* (2006.01)
 *G01N 33/68* (2006.01)

(52) U.S. Cl.
 CPC ....... *C12Q 1/6804* (2013.01); *C12N 15/1003* (2013.01); *G01N 33/689* (2013.01); *C12Q 2522/101* (2013.01)

(58) Field of Classification Search
 None
 See application file for complete search history.

(56) References Cited

U.S. PATENT DOCUMENTS

| | | | |
|---|---|---|---|
| 4,444,879 A | 4/1984 | Foster et al. | |
| 5,075,078 A | 12/1991 | Osikowicz et al. | |
| 5,602,005 A | 2/1997 | Herr et al. | |
| 5,712,172 A | 1/1998 | Huang et al. | |
| 6,194,225 B1 | 2/2001 | Oka et al. | |
| 7,998,676 B2 | 8/2011 | Chakrabarty | |
| 8,017,332 B2* | 9/2011 | Liu | C12N 15/1013 435/6.1 |
| 8,383,422 B2 | 2/2013 | Katada et al. | |
| 8,521,440 B2 | 8/2013 | Hillis et al. | |
| 8,536,100 B2 | 9/2013 | Narz | |
| 2002/0182751 A1 | 12/2002 | Herr et al. | |
| 2005/0032097 A1 | 2/2005 | Garvin | |
| 2005/0176943 A1 | 8/2005 | Nishimune et al. | |
| 2006/0067916 A1 | 3/2006 | Schenk et al. | |
| 2007/0065872 A1 | 3/2007 | Yu et al. | |
| 2007/0141583 A1 | 6/2007 | Li et al. | |
| 2008/0118909 A1 | 5/2008 | Tereba et al. | |
| 2008/0176320 A1 | 7/2008 | Liu | |
| 2008/0261293 A1 | 10/2008 | Garvin | |
| 2008/0318250 A1* | 12/2008 | Gilmer | C07K 16/28 435/7.21 |
| 2009/0042255 A1 | 2/2009 | Liu | |
| 2009/0068671 A1 | 3/2009 | Chakrabarty | |
| 2009/0111185 A1 | 4/2009 | Hillis et al. | |
| 2010/0143878 A1 | 6/2010 | Olson et al. | |
| 2013/0158247 A1 | 6/2013 | Fabis et al. | |
| 2014/0234864 A1 | 8/2014 | Krug | |

FOREIGN PATENT DOCUMENTS

| | | |
|---|---|---|
| WO | 9009802 A1 | 9/1990 |
| WO | 9210569 A1 | 6/1992 |
| WO | 2010120518 A2 | 10/2010 |
| WO | 2012033714 A2 | 3/2012 |
| WO | 2012047726 A1 | 4/2012 |
| WO | 2013064824 A1 | 5/2013 |

OTHER PUBLICATIONS

Balhorn (Genome Biology, 2007, vol. 8, No. 9, pp. 227.1-227.8).*
DNA Extraction (dna.flu.edu, Mar. 15, 2011, pp. 1-15).*
S.Z Bathaie, A.A Moosavi-Movahedi, B Ranjbar, A.A Saboury, A mechanistic study of the histone H1-DNA complex dissociation by sodium dodecyl sulfate, Colloids and Surfaces B: Biointerfaces, vol. 28, Issue 1 Apr. 1, 2003, pp. 17-25, ISSN 0927-7765.
Filippo Rusconi, Édouard Valton, Régis Nguyen, Erick Dufourc, Quantification of Sodium Dodecyl Sulfate in Microliter-Volume Biochemical Samples by Visible Light Spectroscopy, Analytical Biochemistry, vol. 295, Issue 1, Aug. 1, 2001, pp. 31-37, ISSN 0003-2697.
Carter et al., "Lateral Flow Microarrays: A Novel Platform for Rapid Nucleic Acid Detection Based on Miniaturized Lateral Flow Chromatography", Nucleic Acids Research, vol. No. 35, Issue No. 10, pp. 1-11, May 3, 2007.
Norris et al., "Acoustic Differential Extraction for Forensic Analysis of Sexual Assault Evidence", Analytical Chemistry, vol. No. 81, Issue No. 15, pp. 6089-6095, Aug. 1, 2009.
Posthuma-Trumpie et al., "Lateral Flow (Immuno)Assay: Its Strengths, Weaknesses, Opportunities and Threats. A Literature Survey", Anal Bioanal Chem, vol. No. 393, Issue No. 2, pp. 569-582, 2009.
Paradowska et al., "Binding of Histone H4k12ac is Depleted in Promoters of Developmentally Important Genes in Sperm of Subfertile Patients", Springer-Verlag, vol. No. 49, Issue No. 1, pp. 121-122, Sep. 3, 2010.

(Continued)

*Primary Examiner* — Lisa V Cook
(74) *Attorney, Agent, or Firm* — Pabitra K. Chakrabarti

(57) ABSTRACT

A method of capturing a sperm deoxyribo nucleic acid (DNA) in a sample is disclosed. The method includes a step of contacting a lysis solution to the sample that includes at least a sperm cell or a sperm cell lysate to lyse the sperm cell. The sperm cell or sperm cell lysate includes a protamine-DNA complex. The method further includes applying at least a protamine-specific antibody to the lysed sperm cell, wherein the protamine-specific antibody binds to the protamine-DNA complex of the lysed sperm cell to form an antibody-protamine-DNA complex. The method further includes capturing the antibody-protamine-DNA complex; and isolating and detecting the sperm DNA from the captured antibody-protamine-DNA complex.

23 Claims, 7 Drawing Sheets

(56) References Cited

OTHER PUBLICATIONS

Vuichard et al., "Differential DNA Extraction of Challenging Simulated Sexual-Assault Samples: A Swiss Collaborative Study", Investigative Genetics, pp. 1-7, 2011.
PCT Search Report and Written Opinion issued in connection with corresponding Application No. PCT/EP2016/056854 dated Jun. 23, 2016.
Taylor,"Extending the Time to Collect DNA in Sexual Assualt Cases", National Institute of Justice, pp. 1-3, Nov. 27, 2016.

\* cited by examiner

METHODS OF CAPTURING SPERM NUCLEIC ACIDS

FIELD

The invention generally relates to methods of capturing sperm nucleic acids from a biological sample. The invention also relates to methods of capturing sperm deoxyribonucleic acid (DNA) using chromatin immunoprecipitation (CHIP).

BACKGROUND

Sample recovered from a sexual assaulted victim is typically a mixture of different cell types including epithelial cells, erythrocytes, white blood cells, various vaginal flora (such as *Lactobacillus*), sperm cells and bacterial, viral or fungal contaminants. Samples of sexual assaults including but not limited to buccal assault or anal assault may further comprise buccal epithelial cells, buccal flora, intestinal epithelial cells, colon epithelial cells, or other bacterial cells as part of the female components. Capture and detection of sperm DNA from a sample, such as a sexual assault sample are primary requirements for applications, such as forensic applications or diagnostic applications.

Different technologies have been developed to capture and/or detect sperm DNA from a sample, which includes: DNA finger printing to distinguish male DNA using Y chromosome probes, restriction fragment length polymorphism (RFLP) or variable number tandem repeats (VNTR) to determine specific patterns of sperm DNA. Nuclear and cytoplasmic stains may also help to identify a sperm cell, however the staining method relies on the intact shape of the sperm cells, which may not be obtained when present in a sexual assault sample. These methods are complex as they require multiple steps and require significant amount of starting DNA. To achieve desired concentration of starting DNA, variety of techniques have been developed, which may include amplification of target DNA. In amplification, contaminating species may also get amplified and the amplification based detection lacks the specificity for detecting cell source of the amplified DNA. These applications are typically preceded by separation and purification of target DNA from unwanted nucleic acids and contaminants to reduce interference in downstream applications and to achieve desired result. However, the traditional purification or separation methods and the associated techniques are complex, time and labor intensive.

In sperm cells, the histone proteins found in somatic cells are replaced in large part by protamine (PRM 1 and PRM 2), and allow further DNA condensation during sperm maturation. Protamine is uniquely expressed in human sperm relative to other cells in the body and serves as a highly specific factor associated with the DNA in sperm cells. The presence of protamine is highly conserved across species.

Chromatin immunoprecipitation (ChIP) is a well-established method for isolating specific DNA through affinity capture of associated proteins. Traditionally ChIP has been used for transcription factor mapping to active gene promoter regions, and more recently has been adapted for analysis of the epigenome of both DNA and associated histone proteins and their respective modifications. ChIP has been used for isolation of protamine DNA complexes, however, ChIP has never been used for purifying sperm specific DNA from a sample comprising different types of cells.

A simplified method for isolating assailant DNA, specifically DNA from sperm cells, from a sample composed of victim's cells and assailant's cells in mixed sexual assault casework samples for subsequent analysis is highly desirable.

BRIEF DESCRIPTION

One embodiment of a method of capturing a sperm deoxyribo nucleic acid (DNA) in a biological sample, comprises contacting a lysis solution to the biological sample comprising at least a sperm cell or a sperm cell lysate comprising a protamine-DNA complex to lyse the sperm cell; applying at least a protamine-specific antibody to the lysed sperm cell, wherein the protamine-specific antibody binds to the protamine-DNA complex of the lysed sperm cell to form an antibody-protamine-DNA complex; capturing the antibody-protamine-DNA complex; and detecting the sperm DNA from the captured antibody-protamine-DNA complex.

Another embodiment of a method of capturing sperm deoxyribonucleic acid (DNA) in a biological sample, comprises providing the sample comprising at least a sperm cell, a partially lysed sperm cell or a sperm cell lysate, wherein the sperm cell, partially lysed sperm cell or sperm cell lysate comprises a protamine-DNA complex; contacting a lysis solution to the sample to lyse the sperm cell or partially lysed sperm cell; applying at least a protamine-specific antibody to the lysed sperm cell, wherein the protamine-specific antibody binds to the protamine-DNA complex of the lysed sperm cell to form an antibody-protamine-DNA complex; capturing the antibody-protamine-DNA complex by adding a capturing agent; and detecting the sperm DNA from the captured antibody-protamine-DNA complex by a DNA amplification reaction.

In another embodiment, a method of purifying deoxyribo nucleic acid (DNA) from a biological sample, comprises providing the biological sample comprising a protamine-DNA complex; applying at least a protamine-specific antibody to the protamine-DNA complex to form an antibody-protamine-DNA complex; capturing the antibody-protamine-DNA complex using a capturing agent; and purifying DNA from the captured antibody-protamine-DNA complex.

DETAILED DESCRIPTION

Figure 1:
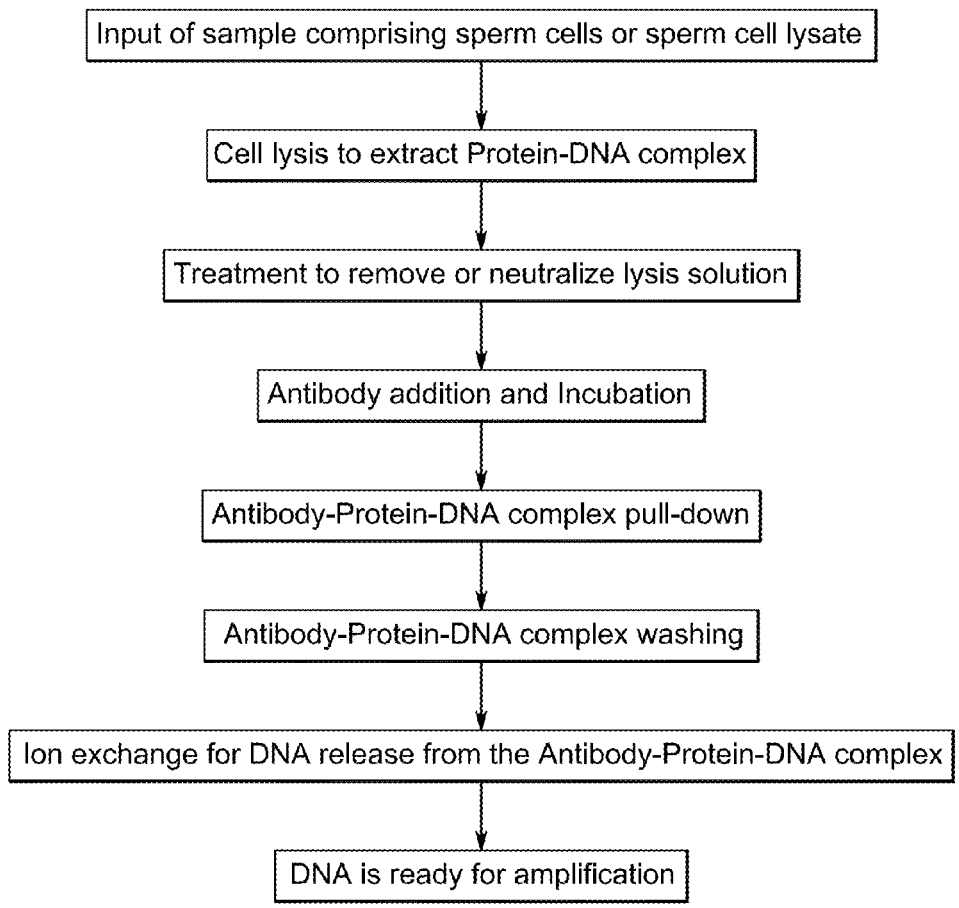
FIG. 1 is a flow chart illustrating the method, in accordance with an example of an embodiment of the invention.

Various embodiments provide suitable methods for capture of target nucleic acids, such as sperm deoxyribo nucleic acid (sperm DNA) from a biological sample comprising non-target nucleic acids, unwanted contaminants. The methods also include detection and analysis of the target nucleic acid. The target nucleic acids are separated from the biological sample by chromatin immune precipitation (ChIP) as a protein-DNA complex, followed by capturing the protein-DNA complex using capturing agent. Finally, the target nucleic acid is isolated from the captured complex followed by detection.

To more clearly and concisely describe the subject matter of the claimed invention, the following definitions are provided for specific terms, which are used in the following description and the appended claims. Throughout the specification, exemplification of specific terms should be considered as non-limiting examples.

The singular forms "a", "an" and "the" include plural referents unless the context clearly dictates otherwise. Approximating language, as used herein throughout the specification and claims, may be applied to modify any quantitative representation that could permissibly vary without resulting in a change in the basic function to which it is related. Accordingly, a value modified by a term such as "about" is not to be limited to the precise value specified. In some instances, the approximating language may correspond to the precision of an instrument for measuring the value. Where necessary, ranges have been supplied, and those ranges are inclusive of all sub-ranges there between.

The term "nucleic acid" as referred to herein comprises all forms of DNA (e.g. genomic DNA, mtDNA) or RNA (mRNA, tRNA, rRNA, small RNA, siRNA, miRNA, non-coding RNA, animal RNA, plant RNA, viral RNA or bacterial RNA), as well as recombinant RNA and DNA molecules or analogues of DNA or RNA generated using nucleotide analogues. The nucleic acids may be single stranded or double stranded. The nucleic acids may include the coding or non-coding strands. The term also comprises fragments of nucleic acids, such as naturally occurring RNA or DNA which may be recovered using the extraction methods disclosed. Nucleic acid may also refer to a portion of a nucleic acid (e.g., RNA or DNA). The extracted nucleic acids may further comprise peptide nucleic acids (PNA).

Captured nucleic acids, such as sperm DNA may be single-stranded, or double-stranded. Molecular weights of captured sperm DNA are also not limited, may be optional in a range from several base pairs (bp) to several mega base pair (Mbp).

As used herein, the term "sperm DNA" refers to a DNA specifically found in male semen sample contributed by the sperm cells. The sperm DNA sequence is of male origin that is desired to be captured by an antibody. The sperm DNA is desired to be detected from a sample comprising multiple cells and contaminants and additionally be amplified in an amplification reaction for further analysis. The sperm DNA may be obtained from a biological sample, such as a bodily fluid (e.g., semen). The sperm DNA may be obtained from any material or biological sample that is contaminated with or contains the sperm DNA, for example fabric, leather, or a tissue, a cell, a cell lysate, a forensic sample, an ancient sample, or a vaginal swab contaminated with the sperm DNA. The biological sample that contains, or is suspected to contain sperm DNA which is obtained from a human origin.

A "template nucleic acid" is defined as a DNA which may be amplified. For example, the template DNA is a sperm DNA captured from a forensic sample. The sperm DNA may be amplified by a DNA polymerase in a DNA amplification reaction to produce amplification products of sperm DNA.

As used herein, the term "capturing agent" refers to a reagent, protein, peptide or nucleic acid that has an affinity towards the protamine specific antibody, which is further bound in a protamine-DNA complex. In some embodiments, the capturing agent is pre-coupled with the primary antibody, which is referred to herein as protamine specific antibody, before apply to the sample. The capturing agent may also be added separately to the sample comprising antibody-protamine-DNA complex. For example, the capturing agent has affinity for "antibody-protamine-DNA complex".

As used herein the dNTP mixture refers to a mixture deoxyribonucleoside triphosphates, where N is a random nucleotide including any of A, C, G, or T/U.

As used herein, "primer", or "primer sequence" refers to a short linear oligonucleotide that hybridizes to a target nucleic acid sequence (e.g., a deoxyribonucleic acid (DNA)) to prime a nucleic acid amplification reaction. The primer may be a ribonucleic acid (RNA) oligonucleotide, a DNA oligonucleotide, or a chimeric sequence. The primer may contain natural, synthetic, or modified nucleotides. Both the upper and lower limits of the length of the primer are empirically determined. The lower limit on primer length is the minimum length that is required to form a stable duplex upon hybridization with the target nucleic acid under nucleic acid amplification reaction conditions. Very short primers (usually less than 3-4 nucleotides long) do not form thermodynamically stable duplexes with target nucleic acids under such hybridization conditions. The upper limit is often determined by the possibility of having a duplex formation in a region other than the pre-determined nucleic acids sequences in the target nucleic acids. As a non-limiting example, suitable primer lengths are often in the range of about 4 to about 40 nucleotides long. A primer may also be used to capture a nucleic acid sequence.

As used herein, the terms "amplification", "nucleic acid amplification", or "amplifying" refer to the production of multiple copies of a nucleic acid template, or the production of multiple nucleic acid sequence copies that are complementary to the nucleic acid template.

As used herein, the term "DNA polymerase" refers to an enzyme that synthesizes a DNA strand de novo using a nucleic acid strand as a template. DNA polymerase uses an existing DNA or RNA as the template for DNA synthesis and catalyzes the polymerization of deoxyribonucleotides alongside the template strand, which it reads. The newly synthesized DNA strand is complementary to the template strand. DNA polymerase can add free nucleotides only to the 3'-hydroxyl end of the newly forming strand. It synthesizes oligonucleotides via transfer of a nucleoside monophosphate from a deoxyribonucleoside triphosphate (dNTP) to the 3'-hydroxyl group of a growing oligonucleotide chain. This results in elongation of the new strand in a 5'→3' direction. Since DNA polymerase can only add a nucleotide onto a pre-existing 3'-OH group, to begin a DNA synthesis reaction, the DNA polymerase needs a primer to which it can add the first nucleotide. Suitable primers comprise oligonucleotides of RNA or DNA or nucleotide analogs. The DNA polymerases may be a naturally occurring DNA polymerases or a variant of natural enzyme having the above-mentioned activity. For example, it may include a DNA polymerase having a strand displacement activity, a DNA polymerase lacking 5'→3' exonuclease activity, a DNA polymerase having a reverse transcriptase activity, or a DNA polymerase having an exonuclease activity.

The term, "reducing agents" as referred to herein include any chemical species that provides electrons to another chemical species. A variety of reducing agents are known in the art. Examples of reducing agents include dithiothreitol (DTT), 2-mercaptoethanol (2-ME), and tris (2-carboxyethyl) phosphine (TCEP). Moreover, any combination of these or other reducing agents may be used. In particular embodiments, the reducing agent is DTT.

The term "amplification buffer" as used herein includes, but is not limited to, 2-Amino-2-hydroxymethyl-propane-1,3-diol (Tris), 2-(N-morpholino) ethanesulfonic acid (MES), 3-(N-morpholino)propanesulfonic acid (MOPS), citrate buffers, 4-(2-hydroxyethyl)-1-piperazineethanesulfonic acid (HEPES), and phosphate buffers. The amplification buffer further includes, for example, Tris-HCl, diammonium sulphate, monovalent cation (such as KCl), divalent cation (such as $MgSO_4$) or Tween®20. This list of potential buffers is for illustrative purposes only. The pH of the buffer is typically titrated in the range of 6 to 8. In some embodiments, the buffer comprises dNTPs, BSA or combination thereof.

The term "separate, separating or separation" used herein indicates the act or action to isolate or purify target nucleic acids, such as sperm DNA from non-target nucleic acid and/or unwanted contaminants of a sample solution.

The term "biological sample" is intended to include a variety of physiological or clinical biological sources that include nucleic acids, specifically sperm DNA. Such sources include, without limitation, tissues, including biopsy materials and aspirates; body fluids such as urine, sputum, semen, secretions and aspirates bacterial cells; and any other source in which DNA may be in. The term "biological sample" is interchangeably used herein as "sample". The sample may be a sexual assault forensics sample, which may have nucleic acids from more than one donor. The sexual assault sample may comprise cells from both victim and assailant. The sample may comprise epithelial cells or epithelial DNA, sperm cells or sperm DNA, bacterial cell or viral cell contaminants, microorganisms or combinations thereof.

The "biological sample comprising at least one sperm cell" is used in a broad sense and intended to include at least a sperm cell, partially lysed sperm cells or sperm cell lysate. In case of sperm cell lysate, the sperm cells are lysed and the cell extract may be present in the sample. In some embodiments, the sample contains sperm head, sperm tail, sperm chromatin, intact sperm cell or combinations thereof. The lysed sperm cell or partially lysed sperm cell is generally present in an old sample. The sample solution is a solution comprising sperm cells, sperm cell components or sperm cell extracts which comprise either or both of DNA and RNA, dissolved, suspended, mixed or otherwise included therein.

As used herein, the term "lysis solution" refers to a solution that is able to lyse the sperm cells. Generally the sperm heads are rich in disulphide bonds and therefore are resistant to traditional lysis. The lysis solution used herein comprises reducing agents and detergents. The lysis solution may comprise dithiothreitol (DTT), tris(2-carboxyethyl) phosphine (TCEP) or combination thereof. The lysis solution may further comprise a detergent selected from sodium dodecylsulphate (SDS). In some embodiments, the presence of SDS shows rapid lysis of the sperm cells, epithelial cells or other different cell types.

One or more embodiments of a method of capturing a sperm DNA from a biological sample are provided. In these embodiments, the method comprises contacting a lysis solution to the biological sample comprising at least a sperm cell or a sperm cell lysate, wherein the sperm cell is lysed in contact with the lysis solution. The sperm cell or sperm cell lysate generally comprises a protamine-DNA complex. On lysis of the sperm cells, the protamine-DNA complex is extracted out from the sperm cells. In these embodiments, the method further comprises applying at least a protamine-specific antibody to the lysed sperm cell (or sperm cell lysate). The protamine-specific antibody binds to the protamine-DNA complex extracted from the lysed sperm cell to form an antibody-protamine-DNA complex. The protamine specific antibody is interchangeably used herein as a "primary antibody". The method further comprises capturing the antibody-protamine-DNA complex and detecting the sperm DNA from the captured antibody-protamine-DNA complex.

FIG. 1 illustrates different method steps encompassing cell lysis, treatment to remove or neutralize excess lysis solution, followed by adding and incubating antibody with the cell lysate to form an antibody-protamine-DNA complex, followed by purification of antibody-protamine-DNA complex using capturing agents, such as secondary antibody or beads. The captured antibody-protamine-DNA complex may be washed, in some embodiments; the captured antibody-protamine-DNA complex is washed repeatedly. The sperm DNA is recovered from the capturing agent by incubating with an ion-exchange resin and the recovered sperm DNA is ready for amplification.

In some embodiments of the method, a lysis solution is added to the sample comprising at least a sperm cell or a sperm cell lysate, wherein the sperm cell or sperm cell lysate comprises a protamine-DNA complex. As noted, the sample may comprise at least a sperm cell, a partially lysed sperm cell or a sperm cell lysate. The live sperm cells or partially lysed sperm cells may be lysed completely by using the lysis solution. The cells are lysed when they are contacted with the lysis solution (or lysis reagents) to extract nucleic acids (sperm DNA) from the sperm cells. In an example of a method, the lysis solution comprises chaotropic substances, detergents and/or other lysis reagents.

The term "lysis solution" may interchangeably be used herein as "lysis reagent". As noted, the lysis solution may comprise chaotropic substances or chaotropes. The examples of chaotropic substances include, but are not limited to, guanidinium hydrochloride, guanidinium chloride, guanidinium isothiocyanate/thiocyanate, sodium thiocyanate, sodium perchlorate, sodium iodide, potassium iodide, urea, and/or any combination thereof. A typical anionic chaotropic series, shown in order of decreasing chaotropic strength, includes: $CCl_3COO^-$, $CNS^-$, $CF_3COO^-$, $ClO_4^-$, $I^-$, $CH_3COO^-$, $Br^-$, $Cl^-$, or $CHO_2^-$. The lysis solution may include chaotropic substances in concentrations of from 0.1 M to 10 M, or from 1 M to 10 M.

In some embodiments, the lysis solution also includes a sufficient amount of buffer. The examples of buffers for use in the lysis solution include tris-(hydroxymethyl) aminomethane hydrochloride (Tris-HCl), sodium phosphate, sodium acetate, sodium tetraborate-boric acid and glycine-sodium hydroxide.

In some embodiments, the lysis solution may also include a non-ionic surfactant, a cationic surfactant, an anionic surfactant, an amphoteric surfactant, and/or any combination thereof. Exemplary nonionic surfactants include, but are not limited to, t-octylphenoxypolyethoxyethanol (TRITON X-100™), (octylphenoxy)polyethoxyethanol (IGEPAL™ CA-630/NP-40), triethyleneglycol monolauryl ether (BRIJ™ 30), sorbitari monolaurate (SPAN™ 20), or the polysorbate family of chemicals, such as polysorbate 20 (i.e., TWEEN™ 20), TWEEN™ 40, TWEEN™ 60 and TWEEN™ 80 (Sigma-Aldrich, St. Louis, Mo.). Examples of cationic surfactants include cetyltrimethylammonium bromide, dodecyltrimethylammonium chloride, tetradecyltrimethylammonium chloride and cetylpyridinium chloride. The concentration of the surfactant in the lysis solution could vary slightly among the different surfactants and depending on the components in the biological sample to be lysed. In some embodiments, the concentration of the surfactant is in a range of from about 0.01% to about 20% by weight.

The lysis solution may comprise a reducing agent, a detergent or combination thereof. In some embodiments, the lysis solution comprises a reducing agent selected from dithiothreitol (DTT), tris(2-carboxyethyl)phosphine (TCEP) or combination thereof. In one embodiment, the lysis solution comprises DTT. The lysis solution may comprise 40 mM DTT. In some embodiments, the lysis solution comprises a detergent selected from sodium dodecylsulphate (SDS). The lysis solution may comprise 0.5% to 2% SDS. In one embodiment, the lysis solution comprises 40 mM DTT, 0.5% to 2% sodium dodecyl sulfate (SDS) or combinations thereof.

Figure 2:
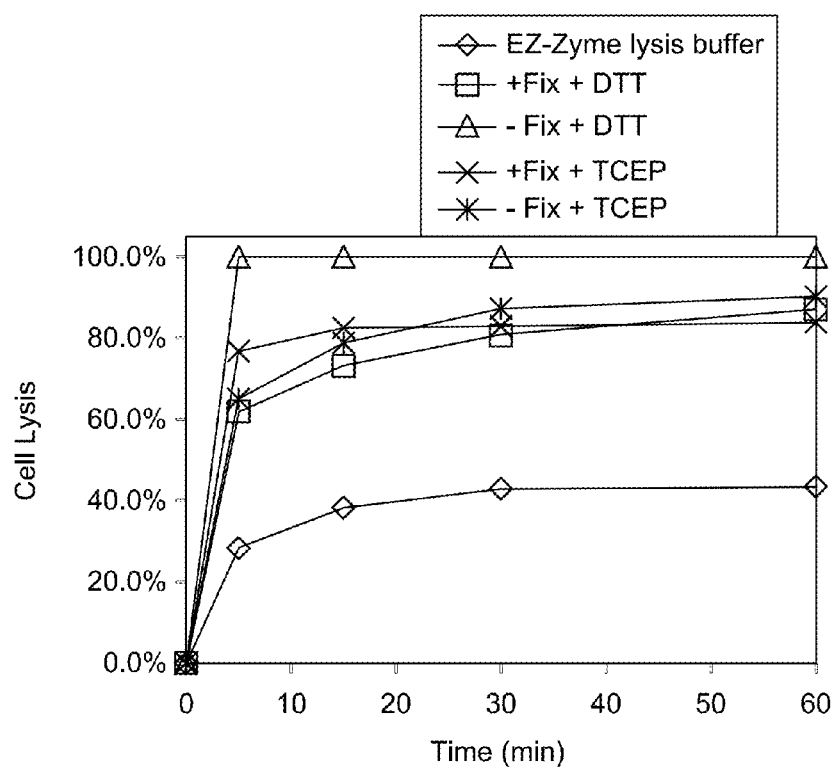
FIG. 2 is a graph showing percent cell lysis with different cell-lysis reagents under different conditions, in accordance with one example of an embodiment of the invention.
Figure 4:
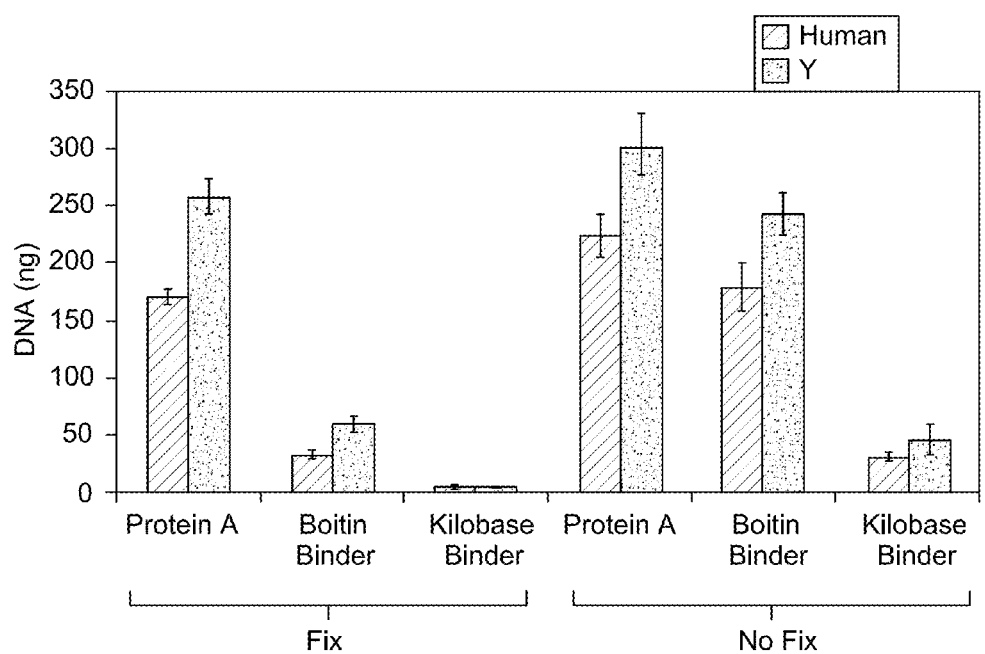
FIG. 4 is a bar graph illustrating DNA yield after pull-down assay under different conditions in accordance with an example of an embodiment of the invention.

The sperm cell heads are rich in disulfide bonds and thereby resistant to traditional lysis. The lysis solution may enable rapid lysis of the sperm cells, wherein the lysis solution comprises detergent such as SDS and/or reducing agent, such as DTT. In some embodiments, the presence of SDS in a lysis solution shows rapid lysis of the sperm cells, epithelial cells or other different cell types. A standard histone-DNA complex is generally disrupted by SDS treatment (S. Z Bathaie, A. A Moosavi-Movahedi, B Ranjbar, A. A Saboury, A mechanistic study of the histone H1-DNA complex dissociation by sodium dodecyl sulfate, Colloids and Surfaces B: Biointerfaces, Volume 28, Issue 1 1 Apr. 2003, Pages 17-25, ISSN 0927-7765). The lysis solution comprising DTT and TCEP was also used to determine the desired reducing agent and optimum lysis conditions (FIG. 2). The addition of DTT to a lysis solution containing SDS showed rapid lysis (in less than 5 min) of sperm cells (FIG. 2). Though the sperm cells were lysed by the lysis solution with SDS, however, surprisingly the protamine-DNA complex was not affected by the use of the same lysis solution, which is an unexpected result, as shown in FIG. 4. In the same experiment, the stabilization of protein-DNA complex was also determined using a fixation reagent, which is typically used for ChIP process. FIG. 4 established the fact that fixation condition is not required for immunoprecipitation of protamine-DNA complex. FIG. 4 further illustrates that the protamine-DNA interaction remains intact and unaffected after repeated washing of the captured antibody-protamine-DNA complex with a buffer containing SDS, which is an unexpected result. The interaction of protamine and DNA is strong enough to withstand SDS treatment, which provides the opportunity to use SDS for sperm cell lysis without disturbing the extracted protamine-DNA interaction.

The antibody-binding and nucleic acid amplification reaction may be affected by one or more inhibitors or contaminants. The contaminants may result from cell lysis, such as cell-debris or other cellular organelle, or the contaminants may be present in the added reagent, such as lysis solution. The contaminants may have inhibitory effect on the downstream processes and need to be removed or neutralized. In some embodiments, the contaminants are removed by washing. In another embodiment, the effect of contaminants is neutralized by adding a reagent. In one embodiment, the excess lysis solution comprising detergent is removed by adding one or more reagents.

In one or more embodiments, the washing step is employed to remove the lysis solution (lysis reagents) from the sample. In some embodiments, the lysis solution comprises SDS, which has an inhibitory effect on the downstream application of antibody binding to the protamine-DNA complex. The SDS also interferes in the amplification reactions using DNA polymerase. In these embodiments, the SDS of the lysis solution is required to be eliminated prior to proceed with an antibody binding and an amplification reaction.

In some embodiments, the method further comprises removing or sequestering the excess lysis solution from a mixture of the sample and the lysis solution after complete lysis of sperm cells. In these embodiments, the excess lysis solution is removed or sequestered prior to applying the protamine-specific antibody to the sample. A mixture forms after adding a lysis solution to the sample, is referred to herein as "post-lysis solution". The post lysis solution generally comprises lysed cells, cell extracts, cell debris, excess lysis solution, excess detergent and other contaminants.

In some embodiments, the removal of excess lysis solution from the post-lysis solution may be achieved by alcohol precipitation of nucleic acids present in the post-lysis solution followed by washing the precipitate. The washed precipitated nucleic acid may be reconstituted to a nucleic acid solution using a buffer. The nucleic acid solution may be incubated with a protamine-specific primary antibody for antibody binding to the protamine-DNA complex.

Figure 3:
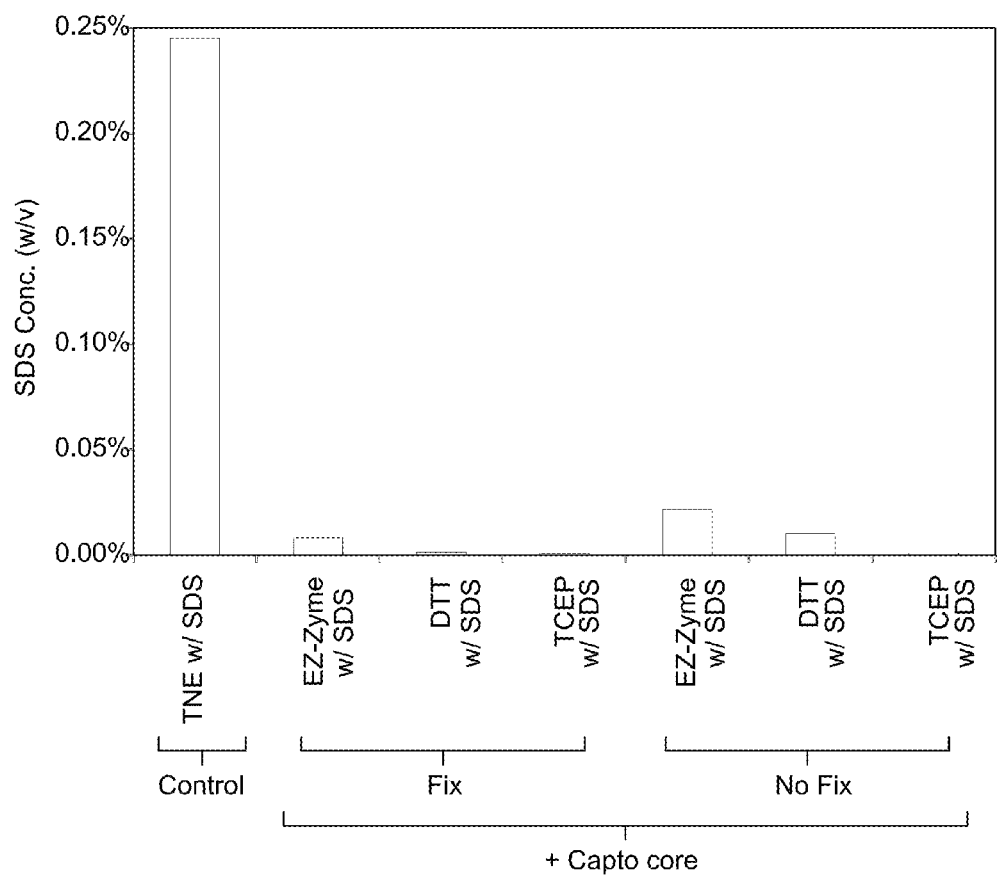
FIG. 3 is a bar graph showing sodium dodecyl sulfate (SDS) sequestration under different conditions in accordance with another example of an embodiment of the invention.

In some embodiments, the detergent of the excess lysis solution is sequestered from the post-lysis solution. In some embodiments, the method further comprises applying a sequestration agent after cell lysis to sequester excess detergent present in the post lysis solution, prior to applying a protamine-specific antibody to the post lysis solution comprising lysed sperm cells. In some embodiments, the sequestration agent comprises ligand-activated core beads coated with size exclusion shell, alpha-cyclodextrin, size exclusion resin or combinations thereof. The example of ligand-activated core beads coated with size exclusion shell is Capto™ core beads (GE HealthCare Life Sciences, Piscataway, N.J.). In these embodiments, the detergent, such as SDS of the lysis solution may be specifically sequestered using different sequestration agents, such as Capto™ core beads, alpha-cyclodextrin, size exclusion resin or combinations thereof. The size exclusion resin may include sephadex G-50, which may be used for sequestering detergent from the post lysis solution. The post lysis solution after sequestration of excess lysis reagent, such as SDS, is referred to herein as "detergent-free sample solution". The term "detergent-free sample solution" refers to substantial removal of the detergent from the solution or the removal is sufficient to bring levels of detergent (SDS) below inhibitory concentrations. The addition of Capto™ core 700 beads to sequester the SDS was sufficient to bring levels of detergent (SDS) below inhibitory concentrations, as shown in FIG. 3.

The lysis of sperm cell results in extraction of the protamine-DNA complex present in the sperm cells. The protamine-DNA complex is the target for protamine specific antibody followed by isolation and detection of sperm DNA form the protamine-DNA complex. Protamine is small, arginine-rich (basic) nuclear protein that mediate normal sperm head condensation and DNA stabilization. The protamine is uniquely expressed in human sperm relative to other cells in the body and as such provides a highly specific factor associated with the DNA found in sperm cells. Typically humans have two or more different protamines, such as protamine 1 (PRM1) and protamine 2 (PRM2). The human protamine 1 gene encodes a 51 amino acid protein and the human protamine 2 gene encodes a 102 amino acid protein. The major proportion of sperm DNA in human is bound to protamines and only a small proportion of DNA bound to histones. Protamine eventually replaces histone late in the haploid phase of spermatogenesis. In matured sperm cells, the DNA forms a complex with protamine, which is referred to herein as a "protamine-DNA complex". The objective of the present method is to capture and separate sperm DNA from the protamine-DNA complex present in the detergent-free sample-solution, which also comprises epithelial cells, other different cell types or cell lysates.

As noted, the method further comprises applying at least a protamine-specific antibody to the detergent-free sample-solution comprising lysed sperm cell. The term "applying" may include, contacting or disposing at least a protamine-specific antibody to the lysed sperm cell using a tube, swab, pipette, catheter, syringe, conduit, an automatic injector, or using any other applicable ways/tools. In some embodiments, the protamine-specific antibody may be poured onto the lysed sperm cell.

The detergent-free sample-solution comprising lysed sperm cell, wherein the lysed sperm cell or sperm cell lysate comprises protamine-DNA complex. The protamine used as an antigen for an antigen-antibody interaction, wherein the antibody employed herein is a protamine-specific antibody (primary antibody). The protamine specific antibody has an affinity for a protein "protamine" and binds to protamine when protamine-specific antibody and protamine are in contact. The protamine-specific antibody, in one or more embodiments, binds to the protamine of the "protamine-DNA complex" extracted from the lysed sperm cell. In these embodiments, the protamine-specific antibody forms an "antibody-protamine-DNA complex".

In some embodiments, the detergent-free sample-solution comprising lysed sperm cell and the protamine-specific antibody needs to be incubated for some time, such as, for 1 hr to 5 hrs under certain conditions to achieve maximum protamine-antibody binding. The protamine-specific antibody may bind to the protamine-DNA complex during incubation at a temperature in a range from about 4° C. to about 37° C. The protamine-specific antibody may bind to the protamine-DNA complex during incubation at 4° C. for a time period in a range from about 10 minutes to about 4 hrs. In some embodiments, the protamine-specific antibody may bind to the protamine-DNA complex during incubation at 4° C. for a time period in a range from about 10 minutes to about 30 mins; in a range from about 10 mins to about 1 hr; in a range from about 10 mins to about 2 hrs; in a range from about 10 mins to about 3 hrs.

In one or more embodiments, the method further comprises capturing the antibody-protamine-DNA complex, wherein the capturing is achieved by using a capturing agent. The capturing agent captures the antibody-protamine-DNA complex present in the detergent-free sample-solution. The term "capture" may include, but is not limited to, physical interaction of the antibody-protamine-DNA complex with the capturing agent, or chemical interaction of the antibody-protamine-DNA complex with the capturing agent. The capturing agent may comprise a secondary antibody, agarose beads, magnetic beads, paramagnetic beads, protein A, streptavidin, sephadex beads, glass beads or combinations thereof. In one embodiment, the capturing agent is a secondary antibody specific to the protamine-specific antibody, wherein the protamine-specific antibody serves as a primary antibody. In one example, protein-A conjugated sepharose CL-4B beads (GE Healthcare) are used to affinity purify the antibody-protamine-DNA complex. In this example, the protein A binds to the antibody present in the antibody-protamine-DNA complex. In another example, goat-anti-rabbit IgG conjugated magnetic beads are used to affinity purify the rabbit anti-protamine IgG-protamine-DNA complex, wherein the goat-anti-rabbit IgG functions as a secondary antibody with respect to the rabbit anti-protamine IgG primary antibody.

In some embodiments, the capturing agent is pre-coupled with the protamine-specific antibody. In these embodiments, the antibody and capturing agent are coupled together before the antibody is applied to the sperm cell lysate (or lysed sperm cell). The term "couple" refers to a physical attachment, chemical attachment, bonding or cross-linking between the capturing agent and the antibody. The antibody and capturing agent may be coupled by a covalent interaction. The functional groups, such as primary amines, sulfhydryl groups and carbohydrates are generally available for antibody modification, for example, labeling, crosslinking or covalent binding.

The protamine specific antibody, which is interchangeably used herein as "primary antibody" may be labeled with a reagent that may be detected easily. In some embodiments, the antibody added to the sample is labelled with a detectable moiety, which may include but is not limited to, an affinity tag, a dye, an enzyme substrate, or a magnetic probe. For example, reagents with maleimide or iodoacetyl groups are effective for sulfhydryl-directed conjugation. Different biotin, fluorescent and enzyme labeling reagents are available which are pre-activated with the maleimide group. In one example, the biotin-conjugated primary antibody is captured by using streptavidin beads. In an illustrative embodiment, the affinity probe is biotin, which is relatively small (244.3 Daltons) ligand and may be conjugated to many proteins and other molecules with minimum alteration of its biological activity. In another embodiment, the biotin tag may be used to facilitate detection using a biotin-binding protein that is conjugated to an enzyme, fluorophore or other reporter molecule. An optimized biotin-to-probe ratio may greatly increase the signal output of a detection system, which provides adequate signal for detection system. The biotin-bound protamine-DNA complex may be purified by centrifugation or physical separation from the sample solution. In another embodiment, the magnetic beads conjugated to anti-protamine IgG is used to capture the protamine-DNA complex. The magnetic bead-bound protamine-DNA complex is then purified from the solution under magnetic field, wherein the magnetic bead-bound and unbound components are separated. In these embodiments, the capturing agents, such as magnetic beads are pre-coupled to the antibody.

In some other embodiments, the capturing of the antibody-protamine-DNA complex is achieved by adding a capturing agent to the detergent-free sample-solution comprising antibody-protamine-DNA complex. In these embodiments, the capturing agent binds to the protamine-specific antibody. As noted, the capturing agents, such as, secondary antibody, agarose beads, magnetic beads, paramagnetic beads, protein A, streptavidin, sephadex beads, glass beads or combinations of two or more of these may be added to the primary antibody (protamine specific antibody)-bound protamine-DNA complex present in the detergent-free sample-solution. The capturing agents have affinity for protamine specific primary antibody and bind to the antibody-protamine-DNA complex. The capturing agent-bound antibody-protamine-DNA complex is referred to herein, as "captured-antibody-protamine-DNA complex".

In some embodiments, the captured-antibody-protamine-DNA complex is washed to remove unbound material and to purify the sperm DNA. In some other embodiments, the method further comprises incubating the captured-antibody-protamine-DNA complex in an ion exchange resin to release and purify the sperm DNA from the captured antibody-protamine-DNA complex. In some embodiments, the captured-antibody-protamine-DNA complex is incubated with the ion exchange resin at 95° C. for at least 10 minutes to release the nucleic acids from the complex. In one embodiment, the captured-antibody-protamine-DNA complex is incubated with the ion exchange resin at 95° C. for about 15 minutes to release the nucleic acids from the complex.

The sperm DNA is captured followed by detection using, for example, detection probes. The capturing agent may comprise a detection probe, or the detection probe may separately be added during, prior or on completion of the purification of the sperm DNA. In one or more embodiments, the detection probe is a reporter moiety, wherein the reporter moiety is coupled to the protamine-specific antibody. In these embodiments, the detection of the reporter moiety indicates the presence of sperm DNA in the sample. The reporter moiety may comprise a chromophore moiety, a fluorescent moiety, a phosphorescence moiety, an affinity probe, a magnetic probe, a paramagnetic probe, a metallic probe or combinations thereof.

The "detection probe" may detect the sperm DNA using one or more detection method. The detection probes may include, but are not limited to, gold particles, antisense oligomer, pyrophosphate, phosphatase, biotin-streptavidin beads, antibody, fluorescence resonance energy transfer (FRET) probes, horseradish peroxidase (HRP) probes and luciferase. The antisense oligomers may comprise of natural nucleotides or nucleotide analogs. The oligonucleotides may be labeled with FRET probes, such as fluorescein, Cy5, Cy5.5, and BIODPY®. In some embodiments, the sperm DNA may be detected by southern blot. The sperm DNA, which is captured and separated, may be detected by colorimetric detection method, chemical, thermal, electrical, pH, luminescence or fluorescence based detection method.

The detection probe may comprise a primary detection probe, a secondary detection probe or a combination thereof. The method further comprises detecting the sperm DNA by using a primary detection probe. In some embodiments, the capturing agent comprises a primary detection probe. The primary detection probe may further comprise a binding moiety such as a biotin or an antibody, a streptavidin, a gold particle or combinations thereof. In different embodiments, the primary detection probe may be coupled to different molecules, substrate, or may be added separately.

In some embodiments, the method further comprises applying a secondary detection probe to the sample solution, wherein the sample already comprises a primary detection probe. In these embodiments, the secondary detection probe binds to the primary detection probe, wherein the primary detection probe previously bound to the antibody-protamine-DNA complex. The primary detection probe or secondary detection probe may comprise a chromophore moiety, a fluorescent moiety, a phosphorescence moiety, an affinity probe, a magnetic probe, a paramagnetic probe or combinations thereof.

In some embodiments, the detection of the sperm DNA is achieved by one or more amplification reactions of the sperm DNA. The method of detection further comprises analyzing the amplified DNA. In amplification reaction, the sperm DNA, isolated from the protamine-DNA complex of the sperm cell sample, is used herein as a template DNA. The amplified sperm DNA may further be analyzed for downstream applications. The detection process may include different forensic analysis of the amplified DNA to identify the assailant.

In one or more embodiments, the sperm DNA is subjected to a nucleic acid amplification reaction that amplifies the sperm DNA present in the sample to form the amplification product or amplicon. The terms "amplification reagent" and "amplification reagent solution" are interchangeably used hereinafter. The amplification reagent comprises a mixture of dNTP's, oligomer (primer), enzyme(s) including polymerase and amplification buffer. In some embodiments, the amplification reaction mixture starts amplification in the presence of the amplification buffer when in contact with the template nucleic acids, which is sperm DNA isolated from protamine-DNA complex. The amplification reagents may also comprise modified nucleotides.

The sperm DNA may be amplified by using a standard polymerase chain reaction (PCR). In some embodiments, the recovered sperm DNA from the captured antibody-protamine-DNA complex is first quantify using a qPCR. In some embodiments, the quantified sperm DNA is then subjected to a multiplex PCR for short tandem repeat (STR) analysis. In some embodiments, the amplification occurs to amplify sperm DNA by an isothermal amplification reaction. The isothermal amplification may include, but is not limited to; rolling circle amplification (RCA), multiple displacement amplification (MDA), helicase dependent amplification (HDA), ping pong amplification, cross priming amplification (CPA), recombinase polymerase amplification (RPA), loop mediated isothermal amplification (LAMP) and strand displacement amplification (SDA).

As noted, the sample comprises at least a sperm cell, lysed sperm cell or sperm cell extract, wherein the sample further comprises epithelial cells, somatic cells, blood cells or combinations thereof. The sample may be a biological sample, which is procured from physiological or clinical biological sources that comprise sperm cells. In one or more embodiments, the sample is selected from a biological sample, a forensic sample, or a biopsy sample. One or more specific examples may include, but is not limited to, a swab, and a semen sample. In some embodiments, the sample may include clothing, a linen, a fabric, a leather that is contaminated with the sperm cells or sperm DNA.

The following examples are included to provide additional guidance to those of ordinary skill in the art in practicing the claimed invention. These examples do not limit the invention as defined in the appended claims.

EXAMPLES

Example 1: Determination of Optimal Cell Lysis Process for Sperm Cells

A lysis solution was added to the sample solution comprising sperm cells or sperm cell lysate. The lysis solution was added and incubated for 1 hr at 37° C. and the process was monitored for 1 hr. Traditional cell lysis for ChIP process employs EZ-Zyme lysis buffer (Millipore, US). Sperm cell heads are rich in disulphide bonds, which make them resistant to traditional lysis using EZ-Zyme lysis buffer. To determine the appropriate lysis solution for sperm cells, a series of lysis solutions was tested.

A lysis solution with DTT and a lysis solution with TCEP were used and the lysis data were compared to determine the better lysis solution for the sperm cells. The lysis process was subjected with pre-fixation (+Fix) or without fixation (−Fix) condition. The fixation is typically performed to stabilize the protein-DNA complex in ChIP process using a reagent, such as formalin. Different lysis conditions were used, including EZ-Zyme lysis buffer (Millipore, US), lysis buffer with DTT under pre-fixation condition, lysis buffer with DTT without fixation condition, lysis buffer with TCEP under pre-fixation condition and lysis buffer with TCEP without fixation condition (as shown in FIG. 2).

Efficient lysis was observed with all reducing conditions relative to traditional lysis for ChIP, however, the most rapid lysis was achieved with DTT and with no fixation condition. The addition of DTT to a lysis buffer containing SDS showed rapid lysis of sperm cells in less than 5 minutes, as shown in FIG. 2. The lysis buffer used for rapid lysis was comprised of 40 mM dithiothreitol (DTT) and 2% sodium dodecyl sulfate (SDS).

Example 2: SDS Sequestration from the Sample Solution

The SDS, due to its inhibitory effect on antibody binding and DNA polymerases functionality, was sequestered prior to proceed with the next step of antibody incubation and binding. Usually Capto™ core ligand binds to small (less than 700 kda) negatively charged molecules over a wide range of pH and salt concentration. Capto™ core 700 (GE Healthcare Life Sciences, Piscataway, N.J.) was used to sequester the SDS molecules and it was proved to be effective in packed bed format. The post lysis solution (a mixture of sample and lysis solution) was mixed with Capto™ core 700 in a 1:1 ratio. The Capto™ core 700 was added to the post lysis solution and was incubated at room temperature for 15 minutes to ensure complete binding of the SDS molecules by Capto™ core 700 beads. After binding the SDS molecules to the beads, the beads were separated from the post lysis solution. SDS concentration was measured using Stains-All dye (Sigma) SDS quantification assay (Filippo Rusconi, Edouard Valton, Regis Nguyen, Erick Dufourc, Quantification of Sodium Dodecyl Sulfate in Microliter-Volume Biochemical Samples by Visible Light Spectroscopy, Analytical Biochemistry, Volume 295, Issue 1, 1 Aug. 2001, Pages 31-37, ISSN 0003-2697). For all conditions, the addition of Capto™ core 700 beads to sequester the SDS was sufficient to bring levels of detergent (SDS) below inhibitory concentrations, as shown in FIG. 3.

For this experiment, different samples were prepared to determine the effect of sequestration agent, such as Capto™ core 700. The control sample comprised of TNE buffer (10 mM Tris pH 8, 100 mM NaCl, and 0.1 mM EDTA) with 0.25% (w/v) of SDS, wherein the sequestration agent Capto™ core 700 was not added. For three test samples, sequestration was done with the sequestration agent Capto™ core 700 in presence of EZ-Zyme lysis buffer (Millipore), TNE with 0.25% (w/v) of SDS and 40 mM DTT, TNE with 0.25% (w/v) of SDS and 40 mM TCEP. Each of the three experimental lysis conditions (test samples) were done in the presence of 1% formalin (+Fix) or no formalin (−Fix), as shown in FIG. 3. FIG. 3 further illustrates the results after treatment with equal volume of Capto™ core 700 beads, wherein the SDS concentration was reduced significantly. It was determined that after sequestration, the concentration of SDS substantially decreased and reached below the inhibitor concentration for DNA amplification.

Example 3: Effect of Fixation on Immunoprecipitation

Formalin fixation is an essential component of conventional ChIP protocol due to the relatively weak interactions of some protein-DNA complexes. The results of cell lysis and DNA sequestration for protamine-DNA complex showed that neither the inclusion nor the exclusion of sample fixation has any direct effect on the process (FIGS. 2 and 3). The effect of formalin fixation was determined on the interaction of protamine and DNA in protamine-DNA complex during immunoprecipitation or capturing using a capturing agent.

Immunoprecipitation

The antibody pull-down assay was performed with Protein A (Life Technologies), Biotin binder (Life Technologies), and Kilobase binder (Life Technologies), wherein the experiments were performed on samples prepared in the presence or absence of fixation agent. The yield of DNA was determined from the immunoprecipitation reactions of pull-down assay. Roughly 17,500 cells were used for this experiment. The cells were either fixed in 1% formalin (+Fix) or no formalin (−Fix). The cells with fixation or without fixation, were incubated with 1 microgram protamine 2 (PRM2) polyclonal antibody (Bioss Inc, US) for the Protien A condition, or biotin conjugated PRM2 polyclonal antibody (Bioss Inc, US) for the Biotin Binder and Kilobase Binder conditions. All samples were incubated at 4° C. for 4 hours in incubation buffer with crowding agent to form antibody-protamine-DNA complex for immunoprecipitation. The incubation buffer with crowding agent comprises 0.001% SDS (s/v), 1.67 mM Tris pH8, 0.11% Triton X-100, 0.12 mM EDTA, 16.7 mM NaCl, 8% Dextran 100 kDa (w/v).

Magnetic Bead Based Antibody Pull-Down Assay

Three varieties of functionalized magnetic beads were used to capture the antibody-protamine-DNA complex. Beads functionalized with Protein A (Life Technologies), and two different beads functionalized with streptavidin, Biotin binder (Life Technologies), and Kilobase binder (Life Technologies) were used according to manufacturer's instructions using a DynaMag™-2 Magnet (Life Technologies) magnetic microcentrifuge tube stand. The captured antibody-protamine-DNA complex (by the application of magnetic beads) was washed five times prior to DNA recovery from the captured antibody-protamine-DNA complex. The captured antibody-protamine-DNA complex was washed sequentially in buffers comprised of 0.01% SDS (w/v), 20 mM Tris pH 8, 1% Triton X-100, 2 mM EDTA, and 500 mM NaCl, 0.01% SDS (w/v), then a second buffer comprised of 20 mM Tris pH8, 1% Triton X-100, 2 mM EDTA 150 mM NaCl, then a third buffer comprised of 250 mM LiCl, 10 mM Tris pH8, 1% NP-40, 1 mM EDTA, 1% Deoxy-cholate, followed by two more washes in 10 mM Tris, pH 8 and 1 mM EDTA. The captured antibody-protamine-DNA complex was then heated to 95° C. for 10 minutes in 10% (w/v) Chelex Resin (Biorad) to release the DNA from the complex. The DNA release from the antibody-protamine-DNA complex is suitable for downstream amplification and was analyzed using Quantifiler Human (ABI) and Quantifiler Y (ABI) kits.

Quantitative Analysis of Recovered Sperm DNA

Recovered DNA yield was quantified using the Quantifiler Human Kit (ABI) for total DNA and Quantifiler Y kit (ABI) for male specific DNA using manufacturer's directions. Since only male specific sperm DNA was used as a sample for this experiment, the use of two quantification methods Quantifiler Human and Quantifilier Y, resulted in a quantification of comparable DNA. The results in FIG. 4 shows the yield of both total DNA (human) and male specific DNA (Y) was higher when fixation was eliminated in all three sets, such as for Protein A, Biotin binder and Kilobase binder. This experiment again established the fact that, while fixation for immunoprecipitation of protamine-DNA complex was performed and the sperm DNA was selectively purified, fixation was not required.

The captured antibody-protamine-DNA complex was washed several times with a buffer composition containing SDS before releasing the DNA. However, the protamine-DNA interaction remains intact and unaffected by SDS treatment, which is an unexpected finding. The interaction of protamine and DNA is strong enough to withstand SDS treatment. This suggests the protocol can be utilized for samples that have either been fixed or not fixed, increasing the sample type that can be used with this protocol.

Qualitative Analysis of Antibody-Protamine-DNA Complex: Western Blot Analysis

The same antibody-protamine-DNA complex samples from the above experiment were subjected to Western blot (FIG. 5) and agarose gel electrophoresis (FIG. 6) for qualitative analysis. The pull-down assay was designed with Protein A, Biotin Binder and Kilobase Binder, as described above. The precipitate was collected from each set after antibody pull-down assay with fixation and without fixation, and the precipitate was subjected to Western blot analysis. The antibody-protamine-DNA complex samples were analyzed on a 4-12% Bis-Tris Protein gradient gel (Invitrogen). The protein from the gel was transferred to a nitrocellulose membrane using a Trans-BlotSD Semi-Dry Transfer Cell (Biorad) according to manufacturer's directions.

Figure 5:
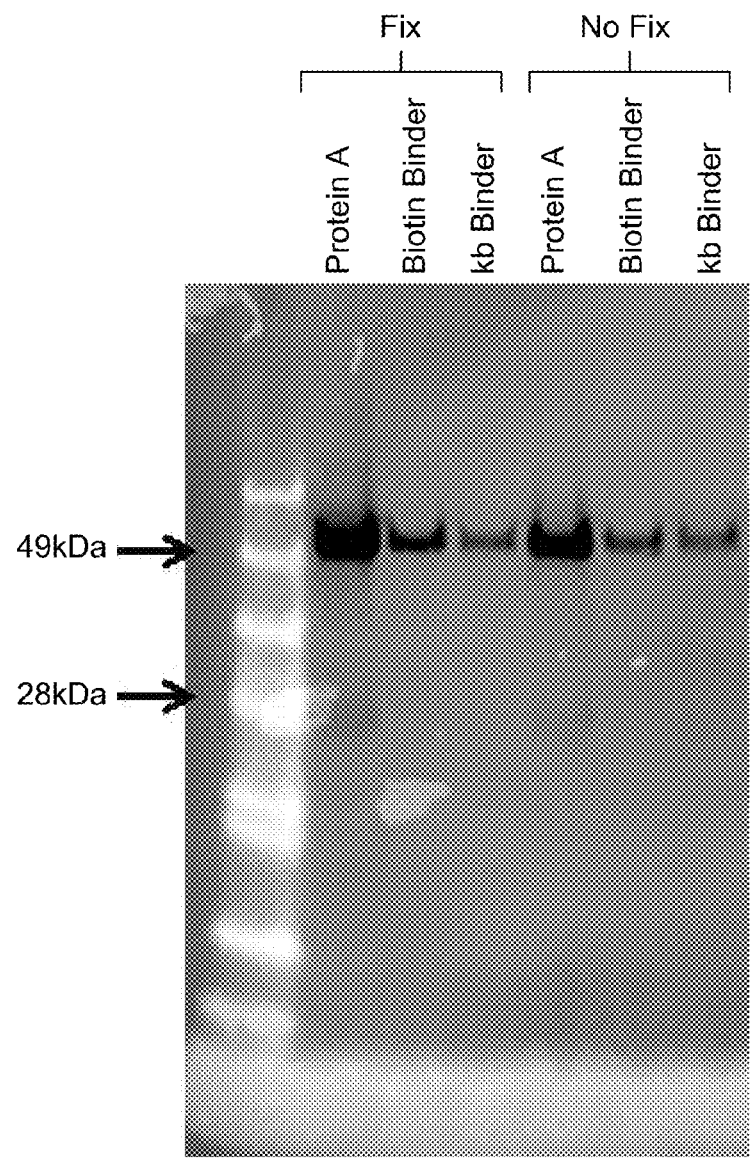
FIG. 5 is an image of a Western blot showing fixation effect on the sample after pull-down assay under different conditions in accordance with an example of an embodiment of the invention.

After transfer, the nitrocellulose membrane was washed with 25 ml TBS (137 mM Sodium Chloride, 20 mM Tris, supplied at pH 7.6.) for 5 minutes at room temperature. The nitrocellulose membrane was incubated in 25 ml of blocking buffer (TBS with 5% non-fat dry milk) for 1 hr at room temperature. The membrane was then washed three times for 5 minutes each with 15 ml of TBST (137 mM Sodium Chloride, 20 mM Tris, 0.1% Tween-20, supplied at pH 7.6). The nitrocellulose membrane was then incubated with a donkey anti-rabbit Cy3 labeled secondary antibody (Jackson Immuno-Research) in 10 ml TBST with gentle agitation for overnight at 4° C. The nitrocellulose membrane was washed for three times for 5 minutes each with 15 ml of TBST. The nitrocellulose membrane was then allowed to dry prior to visualization using Typhoon FLA 9500 (GE Healthcare) according to manufacturer's instructions. FIG. 5 is an image of the blot, which shows bands with same intensity for the samples under fixation or no-fixation conditions. Protein A shows highest efficiency for antibody pull-down assay. Efficient capture of the antibody-protamine-DNA complex in all conditions regardless of fixation was also established by this experiment. The antibody-pull down was not affected by eliminating the fixation step.

Figure 6:
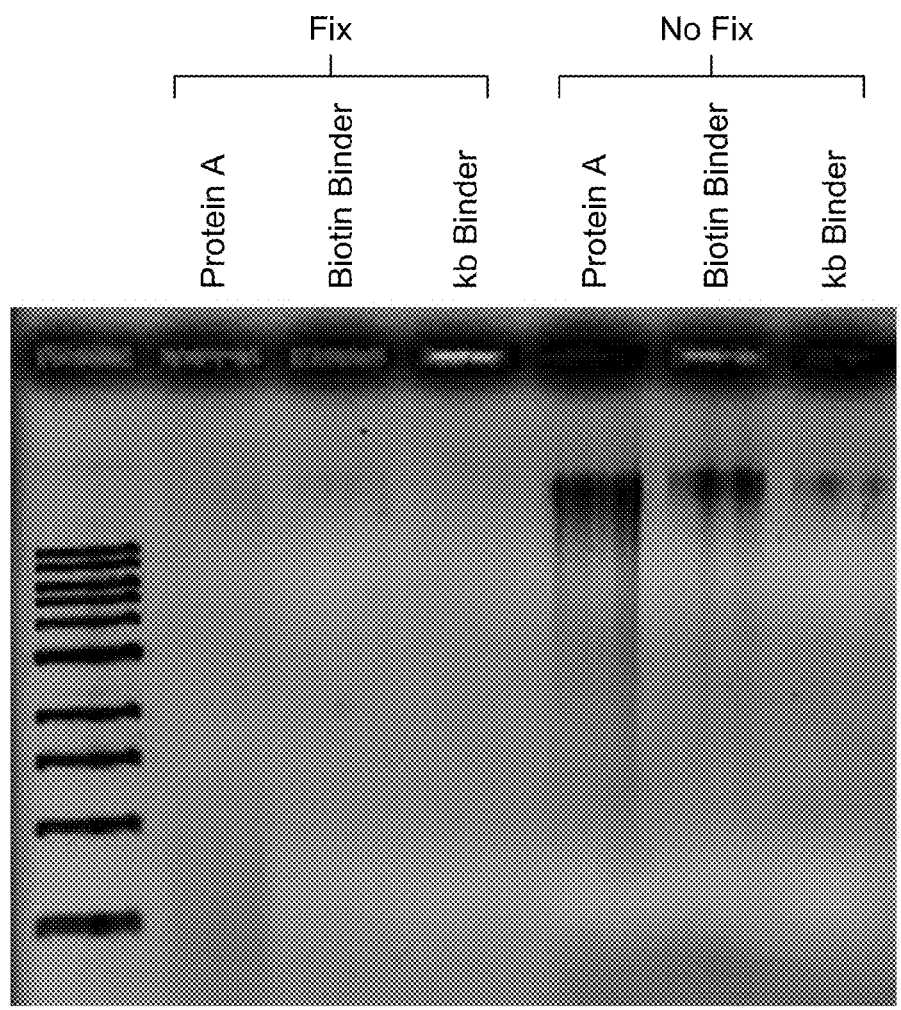
FIG. 6 is a DNA gel electrophoresis image showing fixation effect on the DNA sample recovered from the pull-down assay under different conditions in accordance with an example of an embodiment of the invention.

Qualitative Analysis of Antibody-Protamine-DNA Complex: Agarose Gel Electrophoresis 20 ng DNA samples from the above pull-down assay (FIG. 4) as quantified using a Picogreen assay (Life Technologies) were loaded onto a 1% agarose gel to visually confirm the recovery of DNA and to assess the size of the DNA. The image of DNA gel, FIG. 6, shows that the DNA samples recovered from different sets of pull-down assay treated without fixation, were not degraded as compared to the DNA samples recovered from different sets of pull-down assay treated with fixation conditions. Generally, DNA degrades when DNA is subjected to formalin fixation. As protamine-DNA interaction is comparatively stronger than histone-DNA interaction, the fixation step may not be required for immunoprecipitation of protamine-DNA complex. The removal of fixation step saves time and downstream reverse-cross-linking before purification.

Figure 7:
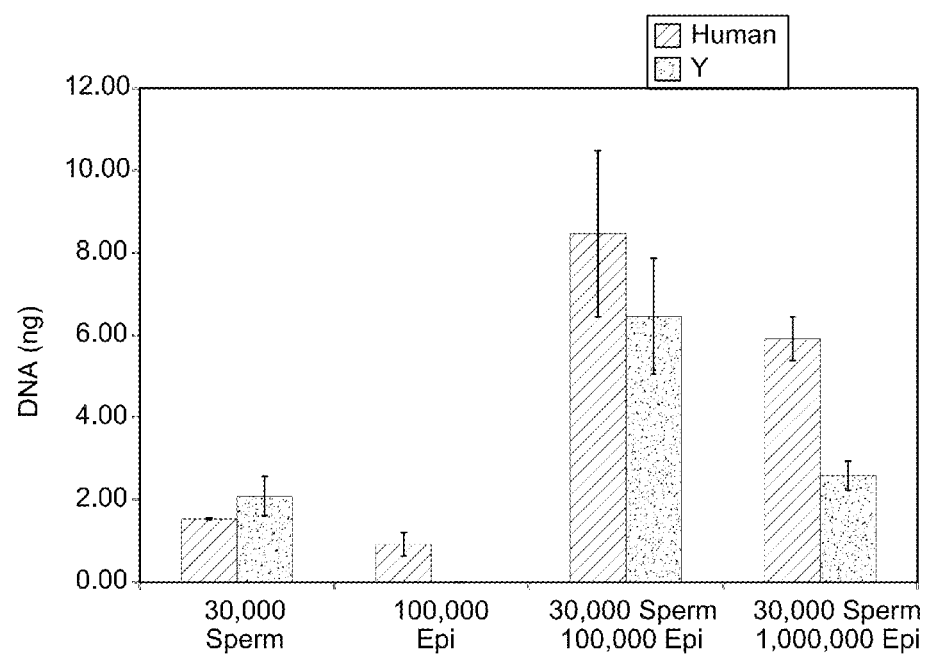
FIG. 7 is a bar graph showing differential capture of sperm DNA from a sample comprising different cell types in accordance with another example of an embodiment of the invention.

Example 4: Differential Capture of Sperm DNA from a Sample Comprising Female Epithelial Cells A sample comprising both sperm cells and female epithelial cells was used for this experiment. Two different samples containing sperm/epithelial cell mixtures were tested in the experiment, in both conditions there were 30,000 sperm cells used while the number of epithelial cells was 100,000 in one sample and 1,000,000 in the other sample. In one control set, only sperm cells were tested and in another control set, only epithelial cells were tested. All samples were prepared with the same workflow that includes rapid lysis using THE w/SDS, excess SDS removal using CaptoCore beads, antibody incubation using crowding agents to form antibody-protamine-DNA complex followed by repeated washing, incubation with Chelex resin to release DNA, and amplification of released DNA using Quantifiler kits (ABI) as previously described. The DNA yield results from this experiment where the samples were composed of both sperm and epithelial cells are shown in FIG. 7.

Differential capture was able to reduce unusable 67:1 female epithelial cells to sperm cells ratio (142:1 DNA ratio) to 2:1. The drastic reduction in DNA template ratio enables the possibility of subtracting the female signature from the profile. STR profile was also generated from the mixed samples (data not shown). Differential capture enables specific capture of sperm DNA from a mixture of completely lysed female epithelial cells and sperm cells.

While the disclosure has been illustrated and described in typical embodiments, it is not intended to be limited to the details shown, since various modifications and substitutions may be made without departing in any way from the spirit of the present disclosure. As such, further modifications and equivalents of the disclosure herein disclosed may occur to persons skilled in the art using no more than routine experimentation, and all such modifications and equivalents are believed to be within the spirit and scope of the disclosure as defined by the following claims.

What is claimed is:

1. A method of detecting a sperm deoxyribo nucleic acid (DNA) in a biological sample, comprising:
   contacting a lysis solution to the biological sample comprising at least a sperm cell or a sperm cell lysate comprising a protamine-DNA complex to lyse the sperm cell, wherein the lysis solution comprises a detergent, and wherein the protamine-DNA complex remains intact after contacting the lysis solution;
   applying a sequestration agent after the sperm cell lysis to sequester an excess detergent of the lysis solution;
   applying at least a protamine-specific antibody to the lysed sperm cell after the sequestration of the excess detergent, wherein the protamine-specific antibody binds to the protamine-DNA complex of the lysed sperm cell to form an antibody-protamine-DNA complex;

capturing the antibody-protamine-DNA complex; and detecting the sperm DNA from the captured antibody-protamine-DNA complex.

2. The method of claim 1, further comprising removing or sequestering the lysis solution prior to applying the protamine-specific antibody.

3. The method of claim 1, wherein the lysis solution comprises a reducing agent, and wherein the reducing agent is selected from dithiothreitol (DTT), tris(2-carboxyethyl) phosphine (TCEP), or a combination thereof.

4. The method of claim 1, wherein the detergent is sodium dodecyl sulfate (SDS).

5. The method of claim 1, wherein the lysis solution comprises 40 mM dithiothreitol (DTT), 0.5% to 2% sodium dodecyl sulfate (SDS), or combinations thereof.

6. The method of claim 1, wherein the sequestration agent comprises ligand-activated core beads coated with size exclusion shell, alpha-cyclodextrin, size exclusion resin, or combinations thereof.

7. The method of claim 1, wherein the protamine-specific antibody binds to the protamine-DNA complex during incubation in a temperature range from 4° C. to 37° C.

8. The method of claim 1, wherein the protamine-specific antibody binds to the protamine-DNA complex during incubation at 4° C. for a time in a range from 10 minutes to 4 hrs.

9. The method of claim 1, wherein the capturing of the antibody-protamine-DNA complex is achieved by a capturing agent, wherein the capturing agent is pre-coupled with the protamine-specific antibody.

10. The method of claim 9, wherein the capturing agent comprises a secondary antibody, agarose beads, paramagnetic beads, protein A, streptavidin, sephadex, glass bead, or combinations thereof.

11. The method of claim 1, wherein the capturing of the antibody-protamine-DNA complex is achieved by further adding a capturing agent, wherein the capturing agent binds to the protamine-specific antibody.

12. The method of claim 11, wherein the capturing agent comprises a secondary antibody, agarose beads, paramagnetic beads, protein A, streptavidin, sephadex, glass bead, or combinations thereof.

13. The method of claim 11, wherein the capturing agent is a secondary antibody specific to the protamine-specific antibody.

14. The method of claim 11, wherein the captured antibody-protamine-DNA complex is washed to remove unbound material and purify the sperm DNA.

15. The method of claim 14, further comprising incubating the captured antibody-protamine-DNA complex in an ion exchange resin.

16. The method of claim 15, wherein the captured antibody-protamine-DNA complex is incubated at 95° C. for at least 10 minutes.

17. The method of claim 1, wherein a reporter moiety is coupled to the protamine-specific antibody and wherein a detection of the reporter moiety indicates the presence of the sperm DNA in the biological sample.

18. The method of claim 17, wherein the reporter moiety comprises a chromophore moiety, a fluorescent moiety, a phosphorescence moiety, an affinity probe, a magnetic probe, a paramagnetic probe, a metallic probe, or combinations thereof.

19. The method of claim 1, wherein the detection of the sperm DNA comprises one or more amplification reactions of the sperm DNA to form an amplified DNA.

20. The method of claim 19, further comprising analyzing the amplified DNA.

21. The method of claim 1, wherein the biological sample further comprises epithelial cells, somatic cells, blood cells, or combinations thereof.

22. The method of claim 1, wherein the biological sample is selected from a forensic sample comprising sperm cells.

23. A method of detecting sperm deoxyribonucleic acid (DNA) in a biological sample, comprising:

providing the biological sample comprising at least a sperm cell, a partially lysed sperm cell or a sperm cell lysate, wherein the sperm cell, partially lysed sperm cell or sperm cell lysate comprises a protamine-DNA complex;

contacting a lysis solution to the biological sample to lyse the sperm cell or partially lysed sperm cell, wherein the lysis solution comprises at least one of a reducing agent and a detergent, wherein the protamine-DNA complex remains intact after contacting the lysis solution;

applying a sequestration agent after the sperm cell lysis to the sample comprising the lysed sperm cells, or the partially lysed sperm cells and an excess of the lysis solution to sequester an excess detergent of the excess of the lysis solution;

applying at least a protamine-specific antibody to the lysed sperm cell after the sequestration of the excess detergent, wherein the protamine-specific antibody binds to the protamine-DNA complex of the lysed sperm cell to form an antibody-protamine-DNA complex;

capturing the antibody-protamine-DNA complex by adding a capturing agent; and detecting the sperm DNA from the captured antibody-protamine-DNA complex by a DNA amplification reaction.

* * * * *